(12) United States Patent
Ducharme

(10) Patent No.: US 8,382,776 B2
(45) Date of Patent: Feb. 26, 2013

(54) MEDICAL DEVICES, SYSTEMS AND METHODS FOR RAPID DEPLOYMENT AND FIXATION OF TISSUE ANCHORS

(75) Inventor: Richard W. Ducharme, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 315 days.

(21) Appl. No.: 12/753,111

(22) Filed: Apr. 2, 2010

(65) Prior Publication Data

US 2010/0256679 A1 Oct. 7, 2010

Related U.S. Application Data

(60) Provisional application No. 61/166,361, filed on Apr. 3, 2009.

(51) Int. Cl.
*A61B 17/04* (2006.01)
(52) U.S. Cl. ...................................................... 606/148
(58) Field of Classification Search .................. 606/139, 606/144, 145, 148, 151, 157, 228, 232
See application file for complete search history.

(56) References Cited

U.S. PATENT DOCUMENTS

| | | | |
|---|---|---|---|
| 2,199,025 A | 4/1940 | Conn | |
| 3,556,079 A | 1/1971 | Omizo | |
| 3,664,345 A | 5/1972 | Dabbs et al. | |
| 3,766,610 A | 10/1973 | Thorsbakken | |
| 3,952,377 A | 4/1976 | Morell | |
| 4,059,333 A | 11/1977 | Mixon, Jr. | |
| 4,235,238 A | 11/1980 | Ogiu et al. | |
| 4,532,926 A | 8/1985 | O'Holla | |
| 4,604,094 A | 8/1986 | Shook | |
| 4,669,473 A | 6/1987 | Richards et al. | |
| 4,719,671 A | 1/1988 | Ito et al. | |
| 5,123,914 A | 6/1992 | Cope | |
| 5,203,787 A | 4/1993 | Noblitt et al. | |
| 5,254,126 A | 10/1993 | Filipi et al. | |
| 5,258,015 A | 11/1993 | Li et al. | |
| 5,282,832 A | 2/1994 | Toso et al. | |
| 5,333,624 A | 8/1994 | Tovey | |
| 5,366,480 A | 11/1994 | Corriveau et al. | |
| 5,383,882 A | 1/1995 | Buess et al. | |
| 5,417,691 A | 5/1995 | Hayhurst | |
| 5,423,860 A | 6/1995 | Lizardi et al. | |
| 5,464,427 A | 11/1995 | Curtis et al. | |
| 5,486,197 A | 1/1996 | Le et al. | |
| 5,520,700 A | 5/1996 | Beyar et al. | |

(Continued)

FOREIGN PATENT DOCUMENTS

| | | |
|---|---|---|
| EP | 0643945 | 3/1995 |
| EP | 0774237 A2 | 5/1997 |

(Continued)

OTHER PUBLICATIONS

International Search Report/Written Opinion for PCT/US2010/029798.

(Continued)

*Primary Examiner* — Ryan Severson
*Assistant Examiner* — Ashley Cronin
(74) *Attorney, Agent, or Firm* — Brinks Hofer Gilson & Lione

(57) ABSTRACT

Medical devices, systems and related methods for delivering a plurality of tissue anchors. The medical devices generally comprise a needle and an over-the-needle suture lock, employed via inner and outer sheaths. The medical systems include a plurality of tissue anchors and at least one biodegradable or resorbable spacer member positioned between adjacent tissue anchors in conjunction with the medical devices.

22 Claims, 5 Drawing Sheets

U.S. PATENT DOCUMENTS

| | | | |
|---|---|---|---|
| 5,527,343 A | 6/1996 | Bonutti |
| 5,531,763 A | 7/1996 | Mastri et al. |
| 5,554,183 A | 9/1996 | Nazari |
| 5,584,835 A | 12/1996 | Greenfield |
| 5,630,824 A | 5/1997 | Hart |
| 5,662,683 A | 9/1997 | Kay |
| 5,690,656 A | 11/1997 | Cope et al. |
| 5,693,060 A | 12/1997 | Martin |
| 5,810,848 A | 9/1998 | Hayhurst |
| 5,865,791 A | 2/1999 | Whayne et al. |
| 5,891,159 A | 4/1999 | Sherman et al. |
| 5,931,844 A | 8/1999 | Thompson et al. |
| 5,948,000 A | 9/1999 | Larsen et al. |
| 5,968,078 A | 10/1999 | Grotz |
| 6,086,608 A | 7/2000 | Ek et al. |
| 6,110,183 A | 8/2000 | Cope |
| RE36,974 E | 11/2000 | Bonutti |
| 6,200,329 B1 | 3/2001 | Fung et al. |
| 6,290,674 B1 | 9/2001 | Roue et al. |
| 6,293,961 B2 | 9/2001 | Schwartz et al. |
| 6,319,271 B1 | 11/2001 | Schwartz et al. |
| 6,328,727 B1 | 12/2001 | Frazier et al. |
| 6,419,669 B1 | 7/2002 | Frazier et al. |
| 6,423,087 B1 | 7/2002 | Sawada |
| 6,432,123 B2 | 8/2002 | Schwartz et al. |
| 6,482,178 B1 | 11/2002 | Andrews et al. |
| 6,491,707 B2 | 12/2002 | Makower et al. |
| 6,551,333 B2 | 4/2003 | Kuhns et al. |
| 6,572,629 B2 | 6/2003 | Kalloo et al. |
| 6,592,559 B1 | 7/2003 | Pakter et al. |
| 6,641,557 B1 | 11/2003 | Frazier et al. |
| 6,699,263 B2 | 3/2004 | Cope |
| 6,712,804 B2 | 3/2004 | Roue et al. |
| 6,746,472 B2 | 6/2004 | Frazier et al. |
| 6,840,953 B2 | 1/2005 | Martinek |
| 6,966,916 B2 | 11/2005 | Kumar |
| 7,025,756 B2 | 4/2006 | Frazier et al. |
| 7,033,379 B2 | 4/2006 | Peterson |
| 7,033,380 B2 | 4/2006 | Schwartz et al. |
| 7,056,325 B1 | 6/2006 | Makower et al. |
| 7,087,073 B2 | 8/2006 | Bonutti |
| 7,115,110 B2 | 10/2006 | Frazier et al. |
| 7,147,652 B2 | 12/2006 | Bonutti et al. |
| 7,217,279 B2 | 5/2007 | Reese |
| 7,300,451 B2 | 11/2007 | Crombie et al. |
| 7,316,706 B2 | 1/2008 | Bloom et al. |
| 7,326,221 B2 | 2/2008 | Sakamoto |
| 7,326,231 B2 | 2/2008 | Phillips et al. |
| 7,335,221 B2 | 2/2008 | Collier et al. |
| 7,371,244 B2 | 5/2008 | Chatlynne et al. |
| 7,390,329 B2 | 6/2008 | Westra et al. |
| 7,416,554 B2 | 8/2008 | Lam et al. |
| 7,494,496 B2 | 2/2009 | Swain et al. |
| 7,601,159 B2 | 10/2009 | Ewers et al. |
| 7,618,426 B2 | 11/2009 | Ewers et al. |
| 7,621,925 B2 | 11/2009 | Saadat et al. |
| 7,622,068 B2 | 11/2009 | Li et al. |
| 7,641,836 B2 | 1/2010 | Li et al. |
| 7,674,275 B2 | 3/2010 | Martin et al. |
| 7,678,135 B2 | 3/2010 | Maahs et al. |
| 7,695,493 B2 | 4/2010 | Saadat et al. |
| 7,704,264 B2 | 4/2010 | Ewers et al. |
| 7,736,376 B2 | 6/2010 | Sato et al. |
| 7,736,378 B2 | 6/2010 | Maahs et al. |
| 7,736,379 B2 | 6/2010 | Ewers et al. |
| 7,744,613 B2 | 6/2010 | Ewers et al. |
| 7,758,598 B2 | 7/2010 | Conlon et al. |
| 7,780,702 B2 | 8/2010 | Shiono |
| 7,785,348 B2 | 8/2010 | Kuhns et al. |
| 7,815,659 B2 | 10/2010 | Conlon et al. |
| 7,815,662 B2 | 10/2010 | Spivey et al. |
| 2004/0147958 A1 | 7/2004 | Lam et al. |
| 2004/0153074 A1 | 8/2004 | Bojarski et al. |
| 2004/0167546 A1 | 8/2004 | Saadat et al. |
| 2004/0186514 A1 | 9/2004 | Swain et al. |
| 2004/0220596 A1 | 11/2004 | Frazier et al. |
| 2005/0113851 A1 | 5/2005 | Swain et al. |
| 2005/0143762 A1 | 6/2005 | Paraschac et al. |
| 2005/0197594 A1 | 9/2005 | Burbank et al. |
| 2005/0251165 A1 | 11/2005 | Vaughan et al. |
| 2005/0251166 A1 | 11/2005 | Vaughan et al. |
| 2005/0277945 A1 | 12/2005 | Saadat et al. |
| 2005/0277957 A1 | 12/2005 | Kuhns et al. |
| 2005/0277981 A1 | 12/2005 | Maahs et al. |
| 2006/0002852 A1 | 1/2006 | Saltzman et al. |
| 2006/0004409 A1 | 1/2006 | Nobis et al. |
| 2006/0004410 A1 | 1/2006 | Nobis et al. |
| 2006/0015006 A1 | 1/2006 | Laurence et al. |
| 2006/0015125 A1 | 1/2006 | Swain |
| 2006/0020274 A1 | 1/2006 | Ewers et al. |
| 2006/0020277 A1 | 1/2006 | Gostout et al. |
| 2006/0025819 A1 | 2/2006 | Nobis et al. |
| 2006/0190016 A1 | 8/2006 | Onuki et al. |
| 2006/0206063 A1 | 9/2006 | Kagan et al. |
| 2006/0217762 A1 | 9/2006 | Maahs et al. |
| 2006/0235447 A1 | 10/2006 | Walshe |
| 2006/0237022 A1 | 10/2006 | Chen et al. |
| 2006/0237023 A1 | 10/2006 | Cox et al. |
| 2006/0241691 A1 | 10/2006 | Wilk |
| 2006/0253144 A1 | 11/2006 | Mikkaichi |
| 2006/0265010 A1 | 11/2006 | Paraschac et al. |
| 2006/0271073 A1 | 11/2006 | Lam et al. |
| 2006/0271101 A1 | 11/2006 | Saadat et al. |
| 2006/0286664 A1 | 12/2006 | McAllister et al. |
| 2007/0010835 A1 | 1/2007 | Breton et al. |
| 2007/0027476 A1 | 2/2007 | Harries et al. |
| 2007/0049970 A1 | 3/2007 | Belef et al. |
| 2007/0093858 A1 | 4/2007 | Gambale et al. |
| 2007/0100375 A1 | 5/2007 | Mikkaichi et al. |
| 2007/0100376 A1 | 5/2007 | Mikkaichi et al. |
| 2007/0112362 A1 | 5/2007 | Mikkaichi et al. |
| 2007/0123840 A1 | 5/2007 | Cox |
| 2007/0162052 A1 | 7/2007 | Hashimoto et al. |
| 2007/0208360 A1 | 9/2007 | Demarais et al. |
| 2007/0213702 A1 | 9/2007 | Kogasaka et al. |
| 2007/0219411 A1 | 9/2007 | Dejima et al. |
| 2007/0255296 A1 | 11/2007 | Sauer |
| 2007/0270752 A1 | 11/2007 | LaBombard |
| 2007/0270889 A1 | 11/2007 | Conlon et al. |
| 2007/0276416 A1 | 11/2007 | Ginn et al. |
| 2007/0276424 A1 | 11/2007 | Mikkaichi et al. |
| 2008/0009888 A1 | 1/2008 | Ewers et al. |
| 2008/0058865 A1 | 3/2008 | Wilk |
| 2008/0065157 A1 | 3/2008 | Crombie et al. |
| 2008/0086153 A1 | 4/2008 | Sakamoto et al. |
| 2008/0114398 A1 | 5/2008 | Phillips et al. |
| 2008/0154290 A1 | 6/2008 | Golden et al. |
| 2008/0172088 A1 | 7/2008 | Smith et al. |
| 2008/0177304 A1 | 7/2008 | Westra et al. |
| 2008/0185752 A1 | 8/2008 | Cerwin et al. |
| 2008/0200930 A1 | 8/2008 | Saadat et al. |
| 2008/0208161 A1 | 8/2008 | Kaji et al. |
| 2008/0208214 A1 | 8/2008 | Sato et al. |
| 2008/0208218 A1 | 8/2008 | Shiono |
| 2008/0208219 A1 | 8/2008 | Suzuki |
| 2008/0208220 A1 | 8/2008 | Shiono et al. |
| 2008/0208251 A1 | 8/2008 | Weadock et al. |
| 2008/0221619 A1 | 9/2008 | Spivey et al. |
| 2008/0228202 A1 | 9/2008 | Cropper et al. |
| 2008/0228203 A1 | 9/2008 | Bell et al. |
| 2008/0243148 A1 | 10/2008 | Mikkaichi et al. |
| 2008/0255422 A1 | 10/2008 | Kondoh et al. |
| 2008/0255423 A1 | 10/2008 | Kondo et al. |
| 2008/0255427 A1 | 10/2008 | Satake et al. |
| 2008/0262525 A1 | 10/2008 | Chang et al. |
| 2008/0269566 A1 | 10/2008 | Measamer |
| 2008/0275297 A1 | 11/2008 | Bakos et al. |
| 2008/0296344 A1 | 12/2008 | Cropper et al. |
| 2008/0300547 A1 | 12/2008 | Bakos |
| 2008/0300627 A1 | 12/2008 | Measamer et al. |
| 2008/0300629 A1 | 12/2008 | Surti |
| 2008/0319257 A1 | 12/2008 | Sato et al. |
| 2009/0005800 A1 | 1/2009 | Franer et al. |
| 2009/0018552 A1 | 1/2009 | Lam et al. |
| 2009/0069847 A1 | 3/2009 | Hashiba et al. |
| 2009/0076527 A1 | 3/2009 | Miyamoto et al. |
| 2009/0088780 A1 | 4/2009 | Shiono et al. |

| | | | |
|---|---|---|---|
| 2009/0088797 A1 | 4/2009 | Crombie et al. | |
| 2009/0125038 A1 | 5/2009 | Ewers et al. | |
| 2009/0125039 A1 | 5/2009 | Mikkaichi et al. | |
| 2009/0204147 A1 | 8/2009 | Rahmani | |
| 2009/0299406 A1 | 12/2009 | Swain et al. | |
| 2009/0326561 A1 | 12/2009 | Carroll, II et al. | |
| 2009/0326578 A1 | 12/2009 | Ewers et al. | |
| 2010/0010457 A1 | 1/2010 | Ewers et al. | |
| 2010/0042115 A1 | 2/2010 | Saadar et al. | |
| 2010/0042144 A1 | 2/2010 | Bennett | |
| 2010/0049213 A1 | 2/2010 | Serina et al. | |
| 2010/0076462 A1 | 3/2010 | Bakos et al. | |
| 2010/0076488 A1 | 3/2010 | Spivey et al. | |
| 2010/0094341 A1 | 4/2010 | Raju | |
| 2010/0106166 A1 | 4/2010 | Cropper et al. | |
| 2010/0113873 A1 | 5/2010 | Suzuki et al. | |
| 2010/0121349 A1 | 5/2010 | Meier et al. | |
| 2010/0174296 A1 | 7/2010 | Vakharia et al. | |
| 2010/0174312 A1 | 7/2010 | Maahs et al. | |
| 2010/0198192 A1 | 8/2010 | Serina et al. | |
| 2010/0211086 A1 | 8/2010 | Ewers et al. | |
| 2010/0268253 A1 | 10/2010 | Ahlberg et al. | |

FOREIGN PATENT DOCUMENTS

| | | |
|---|---|---|
| EP | 1598018 A1 | 11/2005 |
| EP | 1938760 A1 | 7/2008 |
| EP | 2042105 A2 | 4/2009 |
| WO | WO 9904699 | 2/1999 |
| WO | WO 0139671 | 6/2001 |
| WO | WO 0154585 | 8/2001 |
| WO | WO/0158363 | 8/2001 |
| WO | WO 03001893 | 1/2003 |
| WO | WO 03077772 | 9/2003 |
| WO | WO 2004071307 | 8/2004 |
| WO | WO 2006/044837 A2 | 4/2006 |

OTHER PUBLICATIONS

International Search Report/Written Opinion for PCT/US2010/029738.
International Search Report/Written Opinion for PCT/US2008/073080.
International Preliminary Report on Patentability for PCT/US2008/073080.
International Search Report/Written Opinion for PCT/US2008/064513.
International Preliminary Report on Patentability for PCT/US2008/064513.
Office Action dated Oct. 29, 2010 in U.S. Appl. No. 12/125,525.
Office Action dated Mar. 23, 2011 in U.S. Appl. No. 12/125,525.
David J. Desilets et al., Article Entitled "Loop-Anchor Purse-String Versus Endoscopic Clips for Gastric Closure: A Natural Orifice Transluminal Endoscopic Surgery Comparison Study Using Burst Pressures", Journal—Gastrointestinal Endoscopy, vol. 70, No. 6, (2009) pp. 1225-1230.

MEDICAL DEVICES, SYSTEMS AND METHODS FOR RAPID DEPLOYMENT AND FIXATION OF TISSUE ANCHORS

CROSS-REFERENCE TO RELATED APPLICATIONS

This application claims the benefit of U.S. Provisional Application Ser. No. 61/166,361 filed on Apr. 3, 2009, entitled "MEDICAL DEVICES, SYSTEMS, AND METHODS FOR RAPID DEPLOYMENT AND FIXATION OF TISSUE ANCHORS," the entire contents of which are incorporated herein by reference.

FIELD OF THE INVENTION

The present invention relates generally to medical devices for placing tissue anchors in bodily walls, such as for closing perforations in tissue.

BACKGROUND OF THE INVENTION

Perforations in bodily walls may be naturally occurring, or formed intentionally or unintentionally. In order to permanently close these perforations and allow the tissue to properly heal, numerous medical devices and methods have been developed employing sutures, adhesives, clips, staples and the like. One class of such devices is commonly referred to as tissue anchors, T-anchors or visceral anchors. Exemplary tissue anchors are disclosed in U.S. Pat. No. 5,123,914, U.S. application Ser. No. 11/946,565, and U.S. Provisional Application No. 61/166,364, entitled "Tissue Anchors and Medical Devices for the Rapid Deployment of Tissue Anchors" to Ducharme, the entire contents of which are incorporated by reference herein.

Multiple tissue anchors may be used to close a perforation. Difficulties arise in sequentially deploying multiple tissue anchors because the distal-most tissue anchor is being pushed directly upon by an adjacent tissue anchor. Thus, as the distal-most tissue anchor is deployed, the proximally adjacent tissue anchor is already partially deployed and can easily fall out of the introduction needle. Moreover, deploying numerous tissue anchors individually can be tedious and time consuming due to reloading the various tissue anchors into the introduction needle and individually deploying the tissue anchors. There is also difficulty in maintaining the position of the device, while a new tissue anchor is loaded and placed back through the device.

Tissue anchors typically include a crossbar or some anchoring member connected to suture. The anchoring member and suture may take many forms, but generally a needle is used to pierce tissue and deliver the anchoring member on one side of the tissue, leaving the suture extending back to the other side of the tissue. The sutures of one or more tissue anchors are collected and connected together, such as through tying the sutures together. Manually tying suture strands together to close a perforation can be very complex and time consuming. For example, a significant level of skill and coordination is required by the medical professional, especially when the perforation and sutures are difficult to access within the body, such as in endoscopic or laparoscopic procedures. The numerous difficulties with manually tying sutures are well documented. In order to address these and other issues of manual suture tying, various automatic suture tying systems have been developed. Unfortunately, such automatic systems are often complex and costly, difficult to use, and limited to use in certain situations.

BRIEF SUMMARY OF THE INVENTION

The present invention provides medical devices, systems, and related methods for delivering tissue anchors. One embodiment of such a medical device, constructed in accordance with the teachings of the present invention, generally comprises a needle having a needle lumen sized to slidably receive a plurality of tissue anchors, each having an anchoring member connected to a suture. The plurality of tissue anchors includes first and second tissue anchors. The needle lumen defines a longitudinal axis. At least one resorbable spacer member is positioned between the first and second tissue anchors within the needle lumen.

In this embodiment, the medical device further includes a suture lock for fixing the sutures after delivery of the tissue anchors. The suture lock includes a plug and a retaining sleeve. The plug has a main body having a first internal wall defining a first internal passageway sized to slidably receive the needle. The retaining sleeve has a tubular body having a second internal wall defining a second internal passageway sized to receive the plug therein and engage the sutures of the plurality of tissue anchors between the plug and the second internal wall of the retaining sleeve. An inner sheath with an inner sheath lumen sized to slidably receive the needle is sized and positioned to abut the plug. Translation of the inner sheath causes the plug to slide over-the-needle. An outer sheath with an outer sheath lumen sized to slidably receive the inner sheath and the plug is sized and positioned to abut the retaining sleeve.

Another embodiment of a medical system, constructed in accordance with the teachings of the present invention, generally comprises at least one tissue anchor having an anchoring member connected to a suture. The medical system further includes a needle having a needle lumen sized to slidably receive the tissue anchor. The needle and needle lumen define a longitudinal axis. A distal end of the needle defines a needle slot sized to receive the suture therein.

In this embodiment, the medical system further includes an over-the-needle suture lock for fixing the suture after delivery of the tissue anchor through tissue. The suture lock includes a plug and a retaining sleeve. The plug has a main body including a grip extending radially therefrom and a first internal wall defining a first internal passageway. The retaining sleeve has a tubular body with a second internal wall defining a second internal passageway sized to receive the plug and its grip therein. The grip is sized to pinch or compress the suture against the second internal wall. Both the first and second internal passageways are sized to slidably receive the needle during delivery of the tissue anchor. An inner sheath is engageable with the plug and has an inner sheath lumen sized to slidably receive the needle. An outer sheath is engageable with the retaining sleeve and has an outer sheath lumen sized to slidably receive the inner sheath and the plug.

A method of delivering a tissue anchor is also provided in accordance with the teachings of the present invention. A medical device, such as one of the devices described above, is provided. The medical device is delivered to a position proximate the tissue. The needle is deployed by translating the needle relative to the inner and outer sheaths. The tissue anchor is deployed by translating the tissue anchor relative to the needle such that the tissue anchor exits the needle lumen. When the medical device includes a plurality of tissue anchors serially aligned within the needle lumen, the step of deploying the tissue anchor is repeated for at least a portion of the plurality of tissue anchors.

BRIEF DESCRIPTION OF THE DRAWINGS

The accompanying drawings incorporated in and forming a part of the specification illustrate several aspects of the present invention, and together with the description serve to explain the principles of the invention. In the drawings.

DETAILED DESCRIPTION OF THE INVENTION

Figure 1:
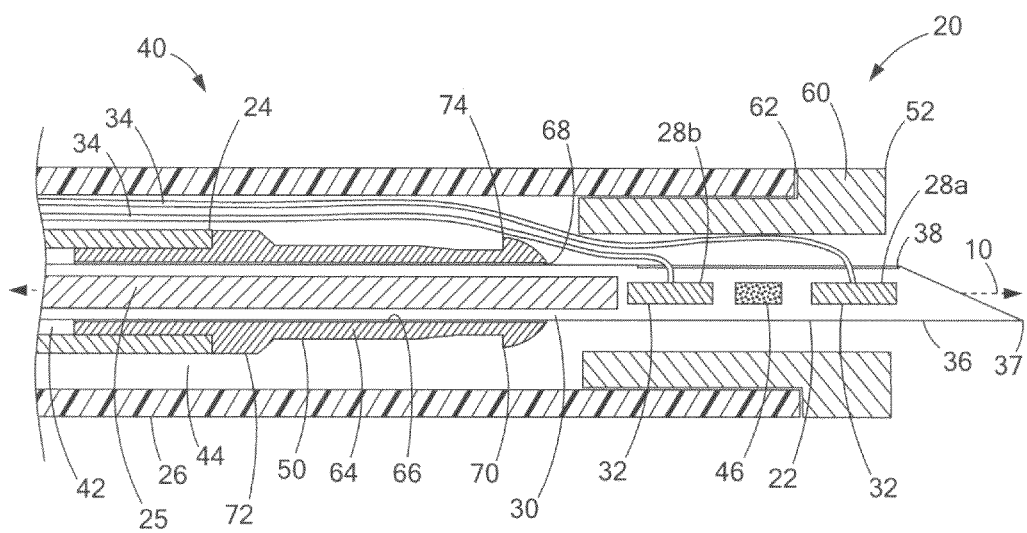
FIG. 1 is a plan view, partially in cross-section, of a medical delivery device constructed in accordance with the teachings of the present invention.
Figure 2:
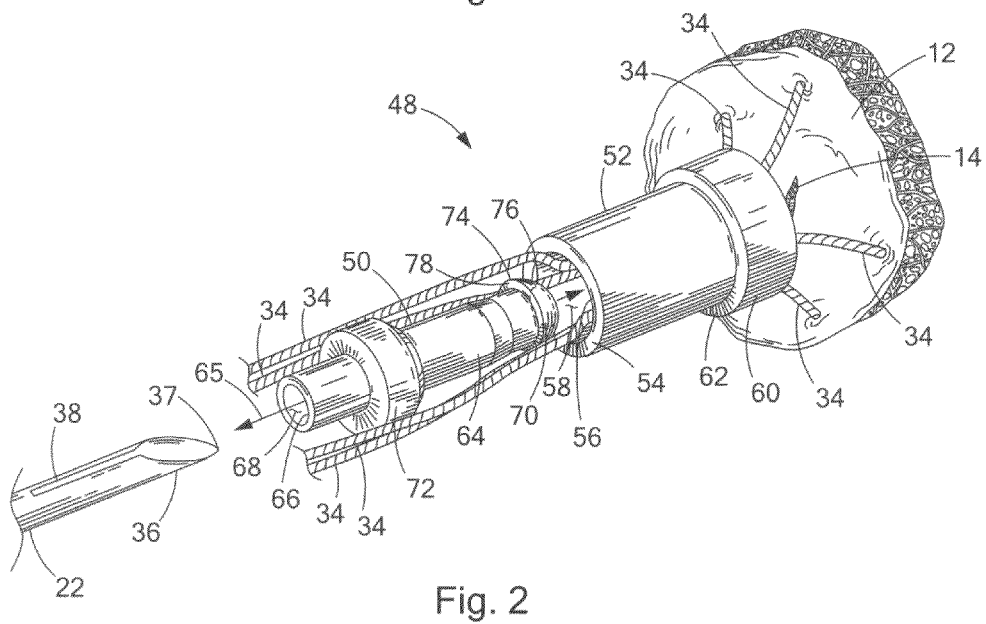
FIG. 2 is a perspective view of a suture lock of a medical delivery device constructed in accordance with the teachings of present invention.

Turning now to the figures, FIG. 1 depicts a medical device 20 constructed in accordance with the teachings of the present invention. The medical device 20 generally comprises a needle 22 and a suture lock 48, which may be employed via inner and outer sheaths 24 and 26. The medical device 20 is designed for delivering tissue anchors 28 through tissue, e.g., for closing a perforation 14, or for apposing tissue, for example, in gastroesophageal reflux disease (GERD) therapy, or bariatric surgery in which an anastamosis is formed, or for use in other procedures. The device 20 preferably includes a pusher 25 extending through the needle 22 for expelling the anchors 28 therefrom.

The tissue anchors 28 and the medical device 20, employed via inner and outer sheaths 24 and 26 and pusher 25, form a medical system 40. That is, the medical device 20 may be utilized with a number of different tissue anchors, and therefore the medical device 20 may be provided separately such that the medical professional may utilize tissue anchors of his or her own choosing. At the same time, the medical device 20 may also be provided with tissue anchors 28 "pre-loaded", thereby forming a medical system 40 in accordance with the teachings of the present invention.

The needle 22 defines a needle lumen 30 and a longitudinal axis 10 of the medical device 20. The needle 22 is preferably constructed of a metal or alloy such as stainless steel or nitinol, although other metals, alloys and plastics can be used for the needle 22, as is known in the art. The needle lumen 30 is sized to slidably receive a plurality of tissue anchors 28 therein. In particular, the tissue anchors 28 generally comprise an anchoring member 32 and a suture 34 attached thereto, and the anchoring member 32 is received within the needle lumen 30 along with a portion of the suture 34. The suture 34 is preferably formed from a flexible material, such as nylon and of the monofilament variety, although the suture 34 may be formed from metal wire, including single filament and multi-filament wires, and wound and braided wires, plastic strings, rope and the like. The suture 34 preferably has a diameter in the range of about 0.20 mm to about 0.35 mm, and most preferably about 0.287 mm, although other sizes may be used and the suture lock 48 sized accordingly.

A distal end 36 of the needle 22 also defines a needle slot 38 that is longitudinally extending and opens longitudinally at the distal end 36 of the needle 22. The slot 38 is sized to receive the sutures 34 therein. The slot 38 may be sized and structured to frictionally engage the sutures 34 therein to provide improved retention of the tissue anchors 28 within the distal end 36 of the needle 22 during manipulation of the needle, e.g., during preparation for a procedure. The slot 38 may have a width sized to be less than or equal to a width of the sutures 34. In this manner, the needle 22 frictionally engages the sutures 34 to retain the tissue anchors 28 within the needle lumen 30. It will be recognized that the needle 22 may not include the slot 38, although it is preferable to keep the sutures 34 safe from the sharp distal tip 37 of the needle 22 through provision of the slot 38, or the width of the slot 38 can be sized larger than a diameter of the sutures 34.

Applicants have discovered that sequentially deploying more than one tissue anchor from the distal end of a needle can lead to improper positioning of the tissue anchors due to proximally arranged tissue anchors prematurely deploying during the deployment of adjacent distally arranged tissue anchors. Accordingly, a biodegradable or resorbable spacer member 46 is preferably positioned between anchoring members 32 of the tissue anchors 28 within the needle lumen 30. While the figures illustrate one spacer member 46 positioned between two tissue anchors 28, it will be recognized by those skilled in the art that a larger number of tissue anchors 28 may be disposed within the needle lumen 30, and thus a larger number of spacer members 46 may likewise be disposed within the needle lumen 30. In addition, more than one spacer member 46 may be positioned between adjacent tissue anchors 28 to provide a larger distance between tissue anchors 28.

As used herein, the term "resorbable" refers to the ability of a material to be absorbed into a tissue and/or body fluid upon contact with the tissue and/or body fluid. A number of resorbable materials are known in the art, and any suitable resorbable material can be used. Examples of suitable types of resorbable materials include resorbable homopolymers, copolymers, or blends of resorbable polymers. Specific examples of suitable resorbable materials include poly-alpha hydroxy acids such as polylactic acid, polylactide, polyglycolic acid (PGA), or polyglycolide; tri-methylene carbonate; polycaprolactone; poly-beta hydroxy acids such as polyhydroxybutyrate or polyhydroxyvalerate; or other polymers such as polyphosphazines, polyorgano-phosphazines, polyanhydrides, polyesteramides, poly-orthoesters, polyethylene oxide, polyester-ethers (e.g., poly-dioxanone) or polyamino acids (e.g., poly-L-glutamic acid or poly-L-lysine). There are also a number of naturally derived resorbable polymers that may be suitable, including modified polysaccharides, such as cellulose, chitin, and dextran, and modified proteins, such as fibrin and casein. Another example of a suitable resorbable material includes bio-remodelable, extracellular matrix material (ECM). One suitable form of ECM is harvested from porcine or bovine small intestine submucosa (SIS). SIS is a resorbable, acellular, naturally occurring tissue matrix composed of ECM proteins in various growth factors. Similarly, a number of biodegradable materials that degrade, but are not necessarily resorbed or adsorbed by the bodily tissues, are known in the art and any suitable biodegradable material can be used.

The longitudinal length of the needle slot 38, which is sized to receive the sutures 34 of the tissue anchors 28 therein, is dependent upon the number of tissue anchors 28 and spacer members 46 within the needle lumen 30 and the lengths of the corresponding anchoring members 32 of the tissue anchors 28 and the spacer members 46. For example, if the anchoring members 32 of the tissue anchors 28 are about the same in length (and if more than one spacer members 46 are used and they are about the same in length), the length of the needle slot 38 may be represented by the following equation:

$$L = L_T(n_T) + L_S(n_S) - \tfrac{1}{2} L_T,$$

wherein L represents the longitudinal length of the needle slot 38, $L_T$ represents the length of the anchoring members 32 of the tissue anchors 28, $n_T$ represents the number of tissue anchors 28 within the needle lumen 30, $L_S$ represents the length of the spacer members 46, and $n_S$ represents the number of spacer members 46 within the needle lumen. Preferably, there is one spacer member 46 positioned between adjacent tissue anchors 28 such that the number of spacer members 46 is one less than the number ($n_T$) of tissue anchors 28. The length of the anchoring members 32 is preferably between around 6 mm and 10 mm, most preferably around 8 mm. The length of the spacer members 46 is preferably between around 3 mm and 6 mm, most preferably around 5 mm. In one preferred construction in which the needle 22 houses two tissue anchors 28 disposed within the needle lumen 30 and one spacer member 46 positioned between the two tissue anchors, the needle 22 has an outer diameter of about 0.042 inches, an inner diameter of about 0.032 inches, and the slot 38 has a longitudinal length of about 12 mm to about 21 mm, and most preferably about 17 mm. In the currently preferred embodiment, two anchors and one spacer are used in the system 40.

The medical device 20 further includes an over-the-needle suture lock 48 for fixing the sutures 34 of the tissue anchors 28 after delivery of the tissue anchors 28 through a bodily wall 12. An over-the-needle suture lock 48, in accordance with the teachings of the present invention, allows the sutures 34 of the tissue anchors 28 to be preloaded within the suture lock 48 during delivery of the tissue anchors 28 through the bodily wall 12. The suture lock 48 generally includes a locking pin or plug 50 and a retaining sleeve 52 which cooperate to fix the sutures 34 of the tissue anchors 28 relative to tissue of the bodily wall 12 for closing the perforation 14 in the bodily wall 12. Although the retaining sleeve 52 and plug 50 have been depicted as having circular cross-sections, it will be recognized that other cross-sectional shapes may be used including triangular, square, etc.

As best seen in FIGS. 2-5, the retaining sleeve 52 generally includes a tubular body 54 having an interior surface 56 defining an interior passageway 58. A peripheral rim 60 is formed at a distal end of the tubular body 54, and defines a shoulder 62 which is used for placement of the retaining sleeve 52, as will be discussed in further detail herein. Generally, the retaining sleeve 52 receives the sutures 34 of the tissue anchors 28 within the interior passageway 58. The sutures 34 are then fixed in place using the plug 50, which is designed to fit within the passageway 58 and pinch or compress the sutures 34. It will also be recognized that the plug 50 may have many configurations (e.g. regular or irregular shapes), and constructions (e.g. cast, molded, machined, wound (such as with wire), etc.) so long as a portion of the plug 50 cooperates with the retaining sleeve 52 to fix the sutures 34.

Figure 3:
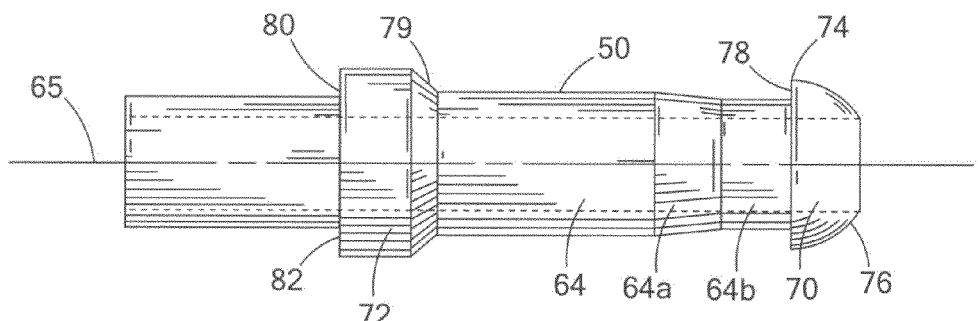
FIG. 3 is a side view of a plug forming a portion of the suture lock depicted in FIG. 2.
Figure 4:
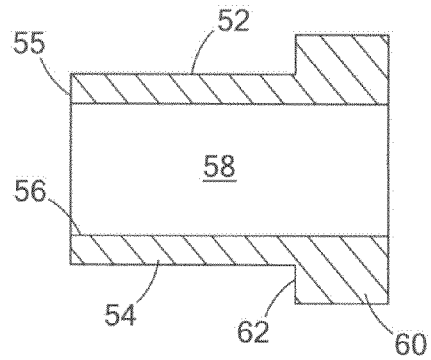
FIG. 4 is a cross-sectional view of a retaining sleeve forming a portion of the suture lock depicted in FIG. 2.

As best seen in FIGS. 2-5, the plug 50 generally includes a main body 64 having an interior surface 66 defining an interior passageway 68 sized to slidably receive the needle 22. The main body 64 and the interior passageway 68 define a longitudinal axis 65. The main body 64 includes a grip 70 and a stop 72, each extending radially from the main body 64. In the illustrated embodiment, the grip 70 is formed at a distal end of the plug 50, although it could be moved proximally along the length of the main body 64. The grip 70 defines an annular edge 74 that is used to engage the sutures 34, as will be discussed in more detail herein. The grip 70 includes a leading surface 76 located distally of the annular edge 74, and a trailing surface 78 located proximally of the annular edge 74. The leading surface 76 tapers, and most preferably is curved such as the dome-shaped surface (e.g., semi-spherical) shown in FIGS. 2-3. At the same time, the trailing surface 78 is generally transverse to the longitudinal axis 65. The leading and trailing surfaces 76, 78 have apertures corresponding to the interior passageway 68 in the plug 50 such that they are annular or ring shaped. While the trailing surface 78 has been shown as perpendicular to the longitudinal axis 65 in the figures, any shape or angle relative to the leading surface 76 which is sufficient to define the annular edge 74 suitable for gripping the sutures 34 is encompassed herein and by the use of the term "transverse." As shown in FIG. 3, the main body 64 also includes a tapered portion 64a and reduced diameter portion 64b located between the grip 70 and the stop 72.

The stop 72 is longitudinally spaced from the grip 70 and is used to control the position of the plug 50 within the retaining sleeve 52. The stop 72 generally includes a distally facing surface 79 and a proximally facing surface 80. The proximally facing surface 80 and the main body 64 define a shoulder 82 which is used to position the plug 50, as will be discussed in more detail herein. The stop 72 is positioned relative to the grip 70 to prevent the grip 70 from passing completely through the internal passageway 58 of the retaining sleeve 52.

Figure 5:
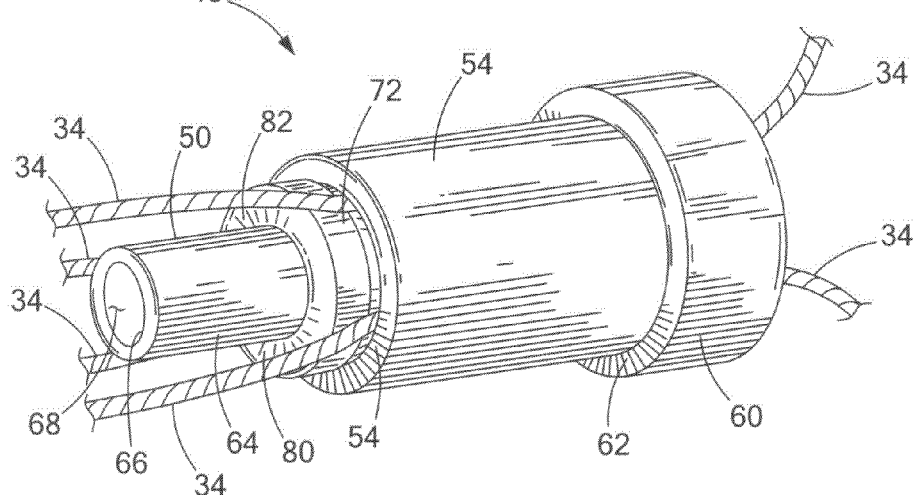
FIG. 5 is a perspective view of the suture lock depicted in FIG. 2, showing the suture lock in a locked configuration.
Figure 9:
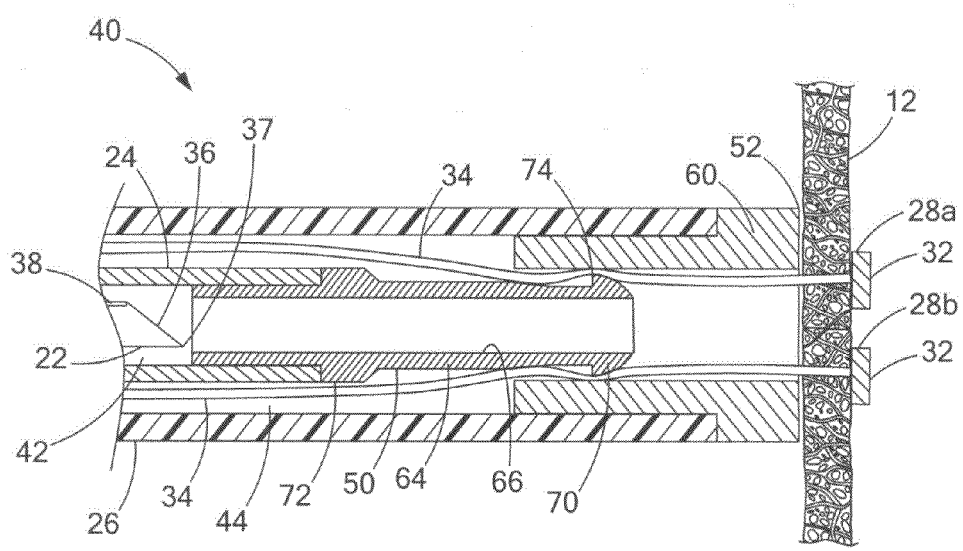
Figure 10:
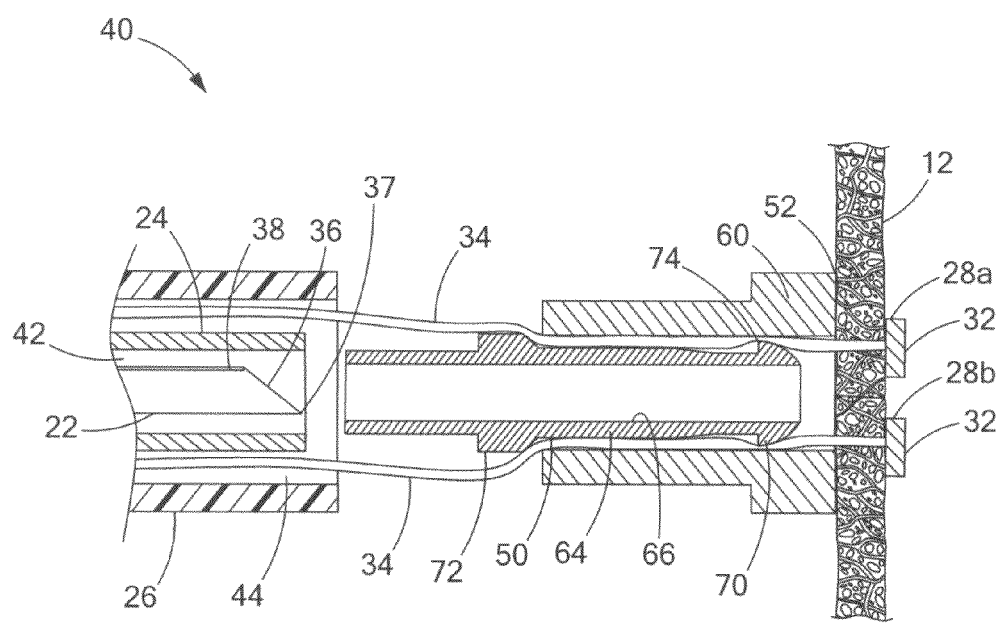

Interconnection of the plug 50 and retaining sleeve 52 will now be described with reference to FIGS. 5 and 9-10, which depict a locked configuration of the suture lock 48 (the unlocked configuration being shown in FIGS. 1-2 and 6-8). Generally, the interior passageway 58 of the retaining sleeve 52 is sized to receive at least a portion of the plug 50 therein. In the locked configuration, the main body 64 and grip 70 are received within the interior passageway 58 of the retaining sleeve 52. As best seen in FIG. 10, the sutures 34 are compressed between the grip 70 and the interior surface 56 of the tubular body 54. As the plug 50 is advanced (i.e. distally) from left to right in FIGS. 9-10, the tapered leading surface 76 of the grip 70 allows the plug 50 to be translated distally relative to the sutures 34 and retaining sleeve 52. However, due to the generally sharp annular edge 74, it is more difficult to move the sutures 34 distally relative to the plug 50. In this manner, the sutures 34 are maintained in a fixed relationship relative to one another and to the tissue of the bodily wall 12.

As will be described in more detail herein, the sutures 34 are generally in tension, due in part to the natural elasticity of the bodily tissue 12, which generally attempts to pull the sutures 34 distally. Accordingly, while the plug 50 may be advanced through the retaining sleeve 52 and slid alongside the sutures 34 into the locked configuration, the tension on the sutures 34 also exerts a distally directed force on the plug 50 via the grip 70 and its annular edge 74. As such, the suture lock 48 is a form of self-motivating locking device that promotes secure fixation of the sutures 34 relative to the tissue 12. At the same time, the sutures 34 may be pulled in the proximal direction to adjust suture tension, suture lock position, and/or perforation closure, even when the suture lock 48 is in the locked configuration.

It can also be seen in FIG. 10 that the main body 64 is sized to at least partially compress the sutures 34 against the interior surface 56 of the tubular body 54. At the same time, the tapered portion 64a and reduced diameter portion 64b provide an area of limited or no contact with the sutures 34. These areas may be sized to adjust the level of friction between the sutures 34 and the suture lock 48, for example based on the type and size of suture material. The stop 72 abuts against a proximal end surface 55 of the tubular body 54, thereby limiting the position of the plug 50 within the retaining sleeve 52. The distally facing surface 79 of the stop 72 is generally tapered to slightly compress the sutures 34 against the tubular body 54, while still allowing the sutures 34 to exit the suture lock 48 and be translated in a proximal direction.

The components of the suture lock 48 may be constructed of various materials, such as stainless steel, titanium, nitinol or other metals/alloys, although various ceramics or plastics can also be employed, such as polycarbonates (PC), polyamides including Nylon™, polytetrafluorethylenes (i.e. PTFE and EPTFE), polyethylene ether ketones (PEEK), polyvinylchlorides (PVC), polyimides, polyurethanes, and polyethylenes (high, medium or low density), including multi-layer or single layer constructions with or without reinforcement wires, coils or filaments. In one preferred construction, the plug 50 has a length of about 0.259 in, the main body 64 has an outer diameter of about 0.065 in along a center region and an outer diameter of about 0.060 in along a proximal region (which is received within the inner sheath 24) and an inner diameter of about 0.045 in defining the interior passageway 68, the stop 72 has an outer diameter of about 0.080 in, and the annular edge 74 defining the grip 70 has an outer diameter of about 0.072 in. In this construction, the retaining sleeve 52 has a length of about 0.150 in, and the tubular body 54 has an outer diameter of about 0.100 in and an inner diameter of about 0.080 in defining the interior passageway 58. While these dimensions of a currently preferred embodiment have been described, the dimensions may be increased or decreased, scaled up or down, to accommodate differently sized anchors, sutures, needles, sheaths, and bodily walls or tissue structures.

The inner sheath 24 defines an inner sheath lumen 42 which is sized to slidably receive the needle 22 therein. The inner sheath 24 is sized and positioned to engage or abut the shoulder 82 of the plug 50. The outer sheath 26 defines an outer sheath lumen 44 which is sized to slidably receive the inner sheath 24 and the plug 50 therein. The outer sheath 26 is sized and positioned to engage or abut the shoulder 62 of the retaining sleeve 52. In one preferred construction, the inner sheath 24 has an outer diameter of about 0.068 in and an inner diameter of about 0.045 in such that the proximal portion of the main body 64 of the plug 50 (having an outer diameter of about 0.060 in) is press fit within the distal end of the inner sheath 24, wherein the inner sheath 24 stretches slightly to hold the plug 50 in place. The plug 50 can then be detached from the inner sheath 24 with a relatively low force. In this preferred construction, the outer sheath 26 has an outer diameter of about 0.131 in and an inner diameter of about 0.095 in such that the tubular body 54 of the retaining sleeve 52 (having an outer diameter of about 0.100 in) is press fit within the distal end of the outer sheath 26, wherein the outer sheath 26 stretches slightly to hold the retaining sleeve 52 in place. The retaining sleeve 52 can then be detached from the outer sheath 26 with a relatively low force.

These dimensions may be increased or decreased, scaled up or down, to accommodate different sized anchors, sutures, needles, suture locks, bodily walls or tissue structures. For example, the inner diameter of the inner and outer sheaths 24 and 26 may be sized larger relative to the plug 50 and retaining sleeve 52, respectively. In this manner, the plug 50 and the retaining sleeve 52 are received by and maintained within the distal ends of the inner and outer sheaths 24 and 26, respectively, by an adhesive or any other suitable means known in the art.

The inner and outer sheaths 24 and 26 are preferably formed of a plastic such as polytetrafluorethylene (PTFE), expanded polytetrafluorethylene (EPTFE), polyethylene ether ketone (PEEK), polyvinylchloride (PVC), polycarbonate (PC), polyamide including nylon, polyimide, polyurethane, polyethylene (high, medium or low density), or elastomers such as Santoprene®, including multi-layer or single layer constructions with or without reinforcement wires, coils or filaments. The needle 22, inner and outer sheaths 24 and 26, and the pusher 25 are preferably elongated structures that are flexible, allowing navigation within a patient's body such as during endoscopic or laparoscopic procedures. As such, a suitable handle or control mechanism will be connected to the proximal ends of the needle 22, inner and outer sheaths 24 and 26, and the pusher 25 for relative translation of these components by the medical professional, as is known in the art. At the same time, the medical devices 20 and systems 40 are also applicable to other tissue anchor placement devices that may be used in open surgery, on external wounds, or that otherwise do not require an elongated medical device to access the targeted tissue.

The medical device 20 may be sized to be used through an accessory channel of an endoscope or alongside an endoscope, or in combination with other devices used in conjunction with endoscopes, for example, endoscopic suction devices or fluid injection devices.

Figure 6:
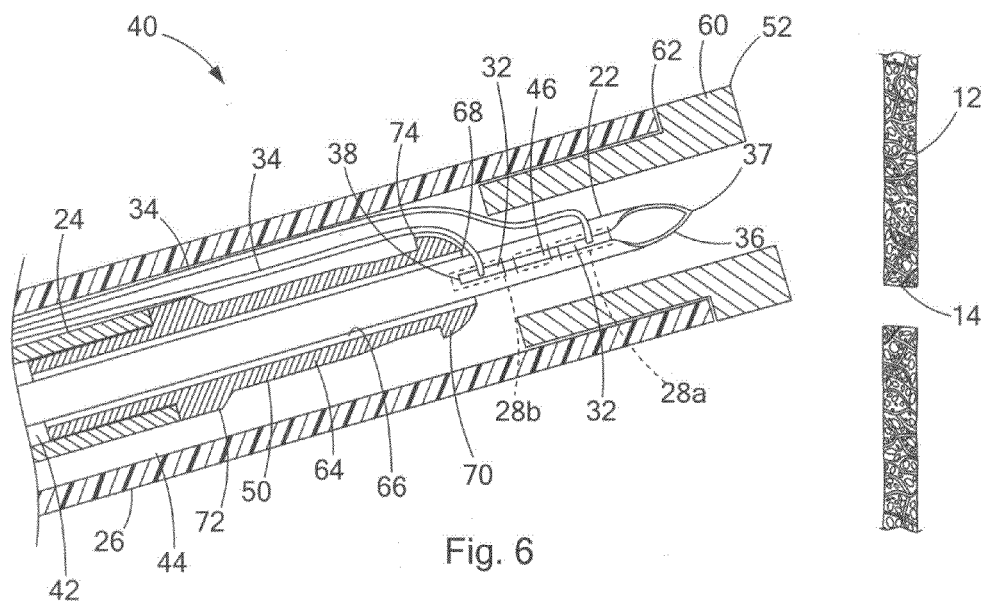
FIGS. 6-10 depict steps in a method for using a medical device in accordance with the teachings of the present invention.
Figure 7:
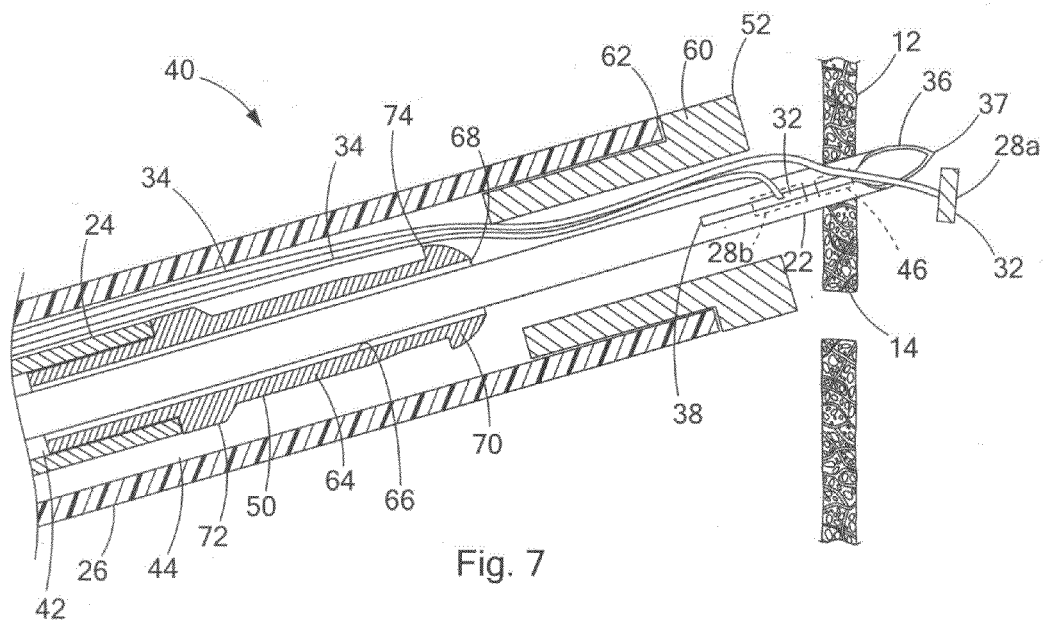
Figure 8:
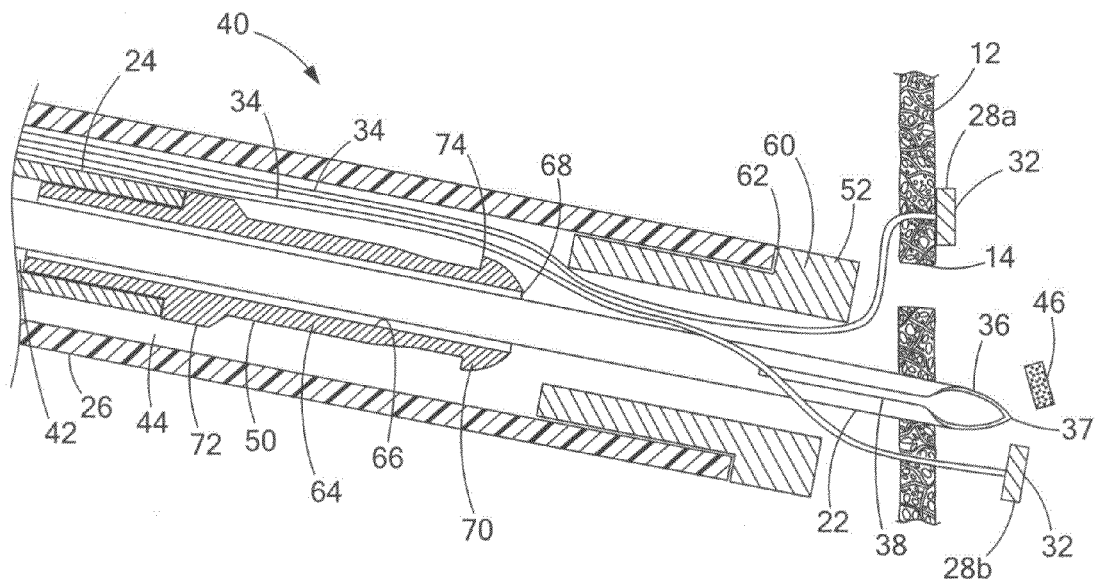

The medical device 20 is operable between at least a delivery configuration, depicted in FIG. 6, and a deployed configuration, depicted in FIGS. 7-8. In the delivery configuration, the needle 22 is substantially contained within the outer sheath lumen 44 so as to protect bodily structures from the sharp distal tip 37 of the needle 22 during introduction of the medical device 20. In the deployed configuration, the needle 22 is translated relative to the inner and outer sheaths 24 and 26 such that the needle 22 projects beyond the distal end 27 of the outer sheath 26. The pusher 25 is translated relative to the needle 22 such that the distal-most tissue anchor 28*a* is urged distally out of the distal tip 37 of the needle 22. The suture 34 connected to the tissue anchor 28*a* also slides distally within the needle slot 38 and exits the needle 22. After deployment of the distal-most tissue anchor 28*a*, the needle 22 is retracted within the outer sheath lumen 44, the medical device 20 is repositioned, and the steps of translating the needle 22 relative to the outer sheath 26 and the pusher 25 relative to the needle 22 are repeated for additional tissue anchors.

A system and method for delivering the tissue anchors 28 through tissue 12 and employing the suture lock 48, in accordance with the teachings of the present invention, will now be described with reference to FIGS. 6-10. The method includes providing a medical system having a plurality of tissue anchors and at least one resorbable spacer member positioned in between adjacent tissue anchors, a needle and inner and outer sheaths, and a suture lock, such as the medical system 40 depicted in FIGS. 1 and 6-10. As shown in FIG. 6, the medical system 40 is delivered to a position proximate the bodily tissue 12 that has been targeted for placement of the tissue anchors 28. The medical system 40 may include a visualization system for assisting in locating the tissue 12, identifying a target site for deployment of the tissue anchors 28, and monitoring operation of the medical device 20 and system 40. For example, visualization techniques may include catheter-based fiber optic systems, fluoroscopy, ultrasound or the like. In addition, the needle 22 can have markings designed for viewing under fluoroscopy, and the distal end 36 of the needle 22 can have a surface of enhanced ultrasonic reflectivity, such by being roughened, having dimples or other incongruities, or having embedded particles.

The tissue anchors 28 are disposed within the needle lumen 30 at the distal end 36 of the needle 22 and a spacer member 46 is disposed between the tissue anchors 28. Spaces between the spacer member 46 and the tissue anchors 28*a* and 28*b* have been shown for clarity, but the spacer member 46 and the tissue anchors 28a and 28b would generally be abutting end-to-end within the needle lumen 30. The sutures 34 follow a somewhat tortuous path from within the needle lumen 30, through the needle slot 38, extending proximally within the outer sheath lumen 44 between the interior surfaces of the retaining sleeve 52 and the outer sheath 26 and the exterior surfaces of the plug and the inner sheath 24, the sutures 34 effectively being preloaded within the suture lock 48 and extending to a proximal end of the medical device 20. Accordingly, this tortuous path can be sufficient to retain the tissue anchors 28 within the needle lumen 30, through frictional engagement of the sutures 34 between the exterior surface of the inner sheath 24 and the interior surface of the outer sheath 26.

The medical device 20 and system 40 are operated into their deployed configuration, as shown in FIG. 7. In particular, the needle 22 is deployed through the bodily tissue 12 by translating the needle 22 relative to the inner and outer sheaths 24 and 26. The distal-most tissue anchor 28a is then deployed from the needle 22 by translating the tissue anchor 28a relative to the needle 22 so that the tissue anchor 28a exits the needle lumen 30. As shown in FIG. 1, the tissue anchors 28 and the spacer member 46 positioned therebetween are shown aligned within the needle lumen 30 along the longitudinal axis 10 of the needle lumen 30 and medical device 20 such that the pusher 25 may be slidably received within the inner sheath lumen 24 and used to engage and press on the proximal-most tissue anchor 28b. Generally, the pusher 25 is advanced distally to press upon the anchoring member 32 of the proximal-most tissue anchor 28b, which will in turn transmit force through the spacer member 46 and the distal-most tissue anchor 28a, thus advancing the distal-most tissue anchor 28a out of the needle lumen 30. It will be recognized by those skilled in the art that other structures or mechanisms can replace the pusher 25 and effectively advance the tissue anchors 28. As the anchoring member 32 of the distal-most tissue anchor 28a is translated distally, the suture 34 connected thereto likewise moves along the needle slot 38 until the entire tissue anchor 28a is freed from the medical device 20, wherein the suture 34 connected to the tissue anchor 28a is released from the needle slot 38.

If, during deployment of the distal-most tissue anchor 28a, the spacer member 46 is moved distally to a position slightly past the needle tip 37, the pusher 25 may be retracted slightly and, due to the adequate clearance between the spacer member 46 and the inner diameter of the needle 22, as the needle pierces the tissue 12, the spacer member 46 is easily moved proximally within the needle lumen 30 to ensure that the sharpened needle tip 37 is able to pierce through the tissue 12 for deployment of the remaining tissue anchors 28.

Turning to FIG. 8, the needle 22 is retracted back through the bodily tissue 12 by translating the needle 22 proximally, repositioned at a different position about the perforation 14, and redeployed back through the tissue 12 by translating the needle 22 relative to the inner and outer sheaths 24 and 26. The pusher 25 is then further advanced distally to deploy the spacer member 46 and the proximal tissue anchor 28b, wherein the suture 34 of the tissue anchor 28b is released from within the needle slot 38. The spacer member 46 may be deployed through the tissue 12 with the proximal tissue anchor 28b, as shown in FIG. 8. Alternatively, the spacer member 46 may be deployed within the body prior to passing the needle 22 through the tissue 12 to deploy the proximal anchor 28b. For example, the spacer member 46 may be deployed within the gastrointestinal tract, wherein the spacer member 46 passes naturally. Since the spacer member 46 is resorbable, it is inconsequential that it is left within the patient's body. Thus, if the spacer member 46 accidentally falls out of the tip 37 of the needle 22 before being deployed with the proximal tissue anchor 28b, this is of no consequence. The proximal tissue anchor 28b is still positioned sufficiently proximal within the needle lumen 30 to be deployed appropriately at the repositioned location. In further embodiments of the invention, the spacer member 46 may contain antibiotics or other drugs, hormones, or growth factors that facilitate healing of the tissue 12 around the implanted tissue anchors 28.

Rather than removing the medical device 20 from the body to reload the needle 22 with additional tissue anchors 28, the medical system 40, in accordance with the teachings of the present invention, provides the ability to sequentially deploy multiple tissue anchors, in which tissue anchors and spacer members disposed between adjacent tissue anchors are preloaded within the needle 22. Accordingly, the longitudinal length of needle slot 38 can be sized to accommodate any number of sutures 34. The method may therefore include withdrawing the needle 22 from the bodily tissue 12 by translating the needle 22 proximally, and then repeating the steps of translating the needle 22 through the tissue 12 and deploying another tissue anchor 28 therethrough.

After the tissue anchors 28 are deployed on the distal side of the bodily tissue 12, the needle 22 is retracted back through to the proximal side of the bodily tissue 12 and retracted within the inner sheath lumen 42. The needle 22 may be removed from within the medical device 20 at this time or it may be removed with the entire medical device 20 after fixation of the sutures 34 relative to the tissue 12. As depicted in FIGS. 9-10, the suture lock 48 is engaged to fix the sutures 34 relative to the bodily tissue 12. Notably, the system 40 again does not require removal from the body, as it includes the over-the-needle suture lock 48. The retaining sleeve 52 is fitted onto the distal end 27 of the outer sheath 26. The outer sheath 26 may take the form of any sheath or catheter known in the art, but preferably has sufficient strength and rigidity for both longitudinal and rotational force transmission, while still providing flexibility for navigation of a patient's body. Exemplary sheaths are sold by Cook Medical, Inc. It will also be recognized that other sheaths or pushing elements may be employed, such as solid wires or wire guides, clamps, graspers and the like. Magnets could likewise be employed to releasably connect the outer sheath 26 to the retaining sleeve 52.

The outer sheath lumen 44 is sized to receive the tubular body 54 of the retaining sleeve 52, while a distal end surface 29 of the outer sheath 26 abuts against the shoulder 62 of the retaining sleeve 52. Generally, the outer sheath 26 and retaining sleeve 52 are loosely press fit such that the retaining sleeve 52 may be readily controlled and positioned using the outer sheath 26. Likewise, the retaining sleeve 52 maintains its connection to the outer sheath 26 during placement of the plug 50 within the retaining sleeve 52, while at the same time the retaining sleeve 52 is also readily disconnected from the outer sheath 26 at the end of the procedure. It will be recognized that the outer sheath 26 and retaining sleeve 52 need not be sized to frictionally engage, as the tensioned sutures 34 and the tissue 12 will generally maintain the position of the retaining sleeve 52 on the outer sheath 52 during placement of the plug 50, such as is shown in FIGS. 9 and 10.

With reference to FIGS. 6-10, the sutures 34 are preloaded or threaded through the interior passageway 58 of the retaining sleeve 52 and through the outer sheath lumen 44. The outer sheath 26 is used to distally translate the retaining sleeve 52 over the sutures 34 to a position proximate the tissue 12 and perforation 14. The sutures 34 are tensioned in order to draw the perforation 14 closed and press the tissue 12 against the peripheral rim 60 of the retaining sleeve 52.

As shown in FIGS. 6-9, the inner sheath 24 is press fit with the plug 50, although the two structures may simply abut each other for longitudinal translation. The inner sheath 24 may have a construction similar to the outer sheath 26 or other catheter described above. In the depicted embodiment, the inner sheath 24 includes a distal end 23 sized to abut against the shoulder 82 and receive the main body 64 of the plug 50, respectively. Accordingly, the inner sheath 24 is connected to the plug 50 and together they are translated distally through the outer sheath lumen 44. If the needle 22 has not yet been withdrawn from the medical device 20 during securing of the sutures 34, the inner sheath 24 causes the plug 50 to slide over-the-needle 22. The plug 50 is pressed into engagement with the retaining sleeve 52 to fix the sutures 34 therebetween. With the sutures 34 in tension (e.g. by pulling them in a proximal direction), the plug 50 is advanced through the interior passageway 58 of the retaining sleeve 52, whereby the sutures 34 are compressed between the grip 70 and the interior surface 56 of the retaining sleeve 52. It can therefore be seen that relative translation of the outer sheath 26 and the inner sheath 24 controls the relative positions of the retaining sleeve 52 and the plug 50 to operate the suture lock 48 between a locked configuration and an unlocked configuration.

As previously discussed, the leading surface 76 of the grip 70 is slid along the sutures 34 as the plug 50 is distally advanced through the interior passageway 56. With further advancement, the main body 64 also engages the sutures 34 and at least partially compresses them against the interior surface 56 of the retaining sleeve 52. The annular shape of the grip 70 allows the sutures 34 to be positioned anywhere around the outer periphery of the grip 70 and plug 50. Distal movement of the plug 50 is eventually limited by the stop 72, and namely the distally facing surface 79 of the stop 72 abutting against the proximal end surface 55 of the retaining sleeve 52. The tension on the sutures 34 grips into the annular edge 74 of the grip 70, and serves to promote movement of the plug 50 in the distal direction, as well as resist proximal movement and unlocking of the suture lock 48.

When in the locked configuration (and when partially locked such as when the plug 50 is partially placed within the retaining sleeve 52 but not fully seated), the grip 70 is structured to permit further translation of the sutures 34 proximally, i.e. away from the tissue 12, and prevent translation of the sutures 34 distally, i.e. towards the tissue 12. Further, the sutures 34 may be individually pulled or tensioned in order to orient the suture lock 48 relative to the bodily tissue 12 and perforation 14, even when the sutures 34 are compressed by the plug 50 and retaining sleeve 52, such as when the suture lock 48 is in the locked configuration. As such, tension on the sutures 34 may be modified to adjust how the perforation 14 is closed. This represents a marked improvement over existing suture locks, which typically are permanently fixed in position along the sutures such that adjustment during and after the locking procedure, i.e. in partially locked and finally locked configurations, is not possible.

In the fully locked configuration, as shown in FIG. 10, the tension on the sutures 34, as well as the natural elasticity of the tissue 12, results in a force being transmitted through the sutures 34 to the grip 70 biasing it in the distal direction. In this manner, the retaining sleeve 52 and plug 50 are interconnected through their respective frictional engagement with the sutures 34 and compression thereof. In the locked condition, the entire medical device 20 may be removed from the patient at once, the inner and outer sheaths 24 and 26 being easily removed from the retaining sleeve 52 and the plug 50, respectively. Alternatively, the inner sheath 24 and needle 22 may be removed first and the outer sheath 26 removed separately. The sutures 34 may be trimmed as necessary with endoscopic scissors and the like. To release the suture lock 48, the sutures 34 may be cut, or the outer sheath 26 may be used to hold the retaining sleeve 52 while the plug 50 is grasped (such as with a snare, forceps, or similar device) and physically withdrawn against the friction and tension of the sutures 34.

Accordingly, the present invention provides a medical system and method capable of delivering multiple tissue anchors in a controlled manner, as well as locking the anchors together (e.g., to close a perforation) without needing to withdraw and introduce the system (or multiple medical devices) any number of times, thereby saving time and improving efficiency. Since the sutures connected to the tissue anchors are preloaded within the over-the-needle suture lock, one medical system is provided for both the delivery of multiple tissue anchors and the fixation of their sutures. The medical system is simple and reliable in use, provides complete perforation closure, and is adaptable to a variety of suture fixation and perforation closure applications. For example, any number of suture strands may be employed and the relative sizes of the plug and retaining sleeve may be adjusted based on suture size, perforation size and the like. The interconnection of the plug and retaining sleeve is such that the suture lock is self-motivated and biased towards a locked configuration, thereby assisting and promoting complete perforation closure as well as control over the position of the suture lock relative to the tissue being sutured through adjustment of the suture strands even when they are compressed. Further description of the interconnection between the plug and retaining sleeve may be found in co-pending U.S. application Ser. No. 12/125,525, the entire contents of which are incorporated by reference herein. Adjustment of individual suture tension and location of the suture lock are also possible during and after placement of the suture lock. At the same time, the inner and outer sheaths provide a simple system for deployment of multiple tissue anchors that can be traversed through the body of a patient to even the most remote locations.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A medical device for delivering a plurality of tissue anchors through tissue, each tissue anchor having an anchoring member connected to a suture, the medical device comprising:
    a needle having a needle lumen sized to slidably receive the plurality of tissue anchors, the needle and the needle lumen defining a longitudinal axis of the medical device, the plurality of tissue anchors including first and second tissue anchors;

at least one spacer member positioned between the first and second tissue anchors within the needle lumen;

a suture lock for fixing the suture after delivery of the tissue anchors, the suture lock comprising,
  a plug having a main body having a first internal wall defining a first internal passageway slidably receiving the needle, and
  a retaining sleeve having a tubular body having a second internal wall defining a second internal passageway slidably receiving the needle and sized to receive the plug therein and sized to engage the suture of the plurality of tissue anchors between the plug and the second internal wall of the retaining sleeve;

an inner sheath having an inner sheath lumen sized to slidably receive the needle, wherein the inner sheath is sized and positioned to abut the plug, wherein translation of the inner sheath causes the plug to slide over-the-needle; and an outer sheath having an outer sheath lumen sized to slidably receive the inner sheath and the plug, wherein the outer sheath is sized and positioned to abut the retaining sleeve.

2. The medical device of claim 1, wherein the plug includes a grip and a stop, the stop extending radially from the main body defining a first shoulder facing proximally, wherein the retaining sleeve includes a peripheral rim extending radially from the tubular body defining a second shoulder facing proximally, wherein the inner sheath is sized and positioned to abut the first shoulder of the plug, and wherein the outer sheath is sized and positioned to abut the second shoulder of the retaining sleeve.

3. The medical device of claim 2, wherein the suture lock is operable between an unlocked configuration during delivery of the plurality of tissue anchors through tissue and a locked configuration after delivery of the plurality of tissue anchors through tissue, the plug and the retaining sleeve being separated in the unlocked configuration and being connected in the locked configuration, the plug and the retaining sleeve sized and structured to compress the suture of the plurality of tissue anchors between the grip of the plug and the second internal wall of the retaining sleeve in the locked configuration.

4. The medical device of claim 1, wherein the first and second tissue anchors include respective first and second anchoring members, the first and second anchoring members and the spacer member being serially aligned within the needle lumen, the medical device further comprising a pusher slidably received within the needle lumen, the pusher sized and positioned to engage the proximal-most anchoring member of the plurality of tissue anchors.

5. The medical device of claim 1, wherein the medical device is operable between a delivery configuration and a deployed configuration, the inner sheath, the plug, and the needle being substantially contained within the outer sheath lumen in the delivery configuration, the needle projecting beyond a distal end of the outer sheath and the retaining sleeve in the deployed configuration.

6. The medical device of claim 1, wherein the suture of the plurality of tissue anchors extends proximally and in between the plug and the retaining sleeve.

7. The medical device of claim 1, wherein the suture of the plurality of tissue anchors extends in a proximal direction along an exterior of the inner sheath and within the outer sheath lumen.

8. The medical device of claim 1, wherein the suture of the plurality of tissue anchors is pre-loaded within the suture lock.

9. The medical device of claim 1, wherein a distal end of the needle defines a needle slot sized to receive the suture of the plurality of tissue anchors therein, the needle slot including a slot length dependent upon the number and the length of the anchoring members of the plurality of tissue anchors and upon the number and length of the spacer members received within the needle lumen.

10. The medical device of claim 1, wherein the plug and retaining sleeve are rigid such that they do not substantially deform or change shape when the retaining sleeve receives the plug to compress the sutures therebetween.

11. The medical device of claim 1, wherein the at least one spacer is distinct from and separable from the plurality of tissue anchors.

12. A medical system comprising:
  at least one tissue anchor, each tissue anchor having an anchoring member connected to a suture;
  a needle having a needle lumen sized to slidably receive the at least one tissue anchor, the needle and needle lumen defining a longitudinal axis, a distal end of the needle defining a needle slot sized to receive the suture therein;
  a suture lock for fixing the suture after delivery of the at least one tissue anchor through tissue, the suture lock including a plug and a retaining sleeve, the plug having a main body including a grip extending radially therefrom and a first internal wall defining a first internal passageway, the retaining sleeve having a tubular body with a second internal wall defining a second internal passageway sized to receive the plug and its grip therein, the grip sized to compress the suture against the second internal wall, both the first and second internal passageways slidably receiving the needle during delivery of the tissue anchor;
  an inner sheath engageable with the plug and having an inner sheath lumen sized to slidably receive the needle; and
  an outer sheath engageable with the retaining sleeve and having an outer sheath lumen sized to slidably receive the inner sheath and the plug.

13. The medical system of claim 12, wherein the suture lock is operable between a locked configuration and an unlocked configuration, the plug and the retaining sleeve being connected in the locked configuration and being separated in the unlocked configuration, the plug and the retaining sleeve sized and structured to compress the suture between the plug and the second internal wall of the tubular body of the retaining sleeve in the locked configuration.

14. The medical system of claim 12, wherein the medical system is operable between a delivery configuration and a deployed configuration, the inner sheath, the plug, and the needle being substantially contained within the outer sheath lumen in the delivery configuration, the needle projecting beyond a distal end of the outer sheath and the retaining sleeve in the deployed configuration.

15. The medical system of claim 12, further comprising a plurality of tissue anchors each having an anchoring member connected to a suture, and wherein the anchoring members are serially aligned within the needle lumen.

16. The medical system of claim 15, further comprising a pusher slidably received within the needle lumen, the pusher sized and positioned to engage the proximal-most anchoring member of the plurality of tissue anchors.

17. The medical system of claim 15, wherein the plurality of tissue anchors includes first and second tissue anchors having first and second respective anchoring members, the medical system further comprising at least one resorbable spacer member disposed between the first and second anchoring members within the needle lumen.

18. The medical system of claim 12, wherein the plug includes a stop extending radially from the main body to define a first shoulder facing proximally and the retaining sleeve includes a peripheral rim extending radially from the tubular body to define a second shoulder facing proximally, wherein the inner sheath engages the first shoulder and the outer sheath engages the second shoulder.

19. A method of delivering at least one tissue anchor through tissue, the tissue anchor having an anchoring member connected to a suture, the method comprising:
providing a medical device comprising a needle, inner and outer sheaths, and a suture lock, the needle having a needle lumen sized to slidably receive the tissue anchor, a distal end of the needle defining a needle slot sized to receive and engage the suture therein, the suture lock including a plug and a retaining sleeve, the plug having a main body with a first internal wall defining a first internal passageway, the retaining sleeve having a tubular body with a second internal wall defining a second internal passageway sized to receive the plug therein, the plug sized to engage the suture within the second internal passageway of the retaining sleeve when in a locked configuration, both the first and second internal passageways sized to slidably receive the needle, the inner sheath engageable with the plug and having an inner sheath lumen slidably receiving the needle, and the outer sheath engageable with the retaining sleeve and having an outer sheath lumen sized to slidably receive the inner sheath and the plug;
delivering the medical device to a position proximate the tissue;
deploying the needle by translating the needle relative to the inner and outer sheaths; and
deploying the tissue anchor by translating the tissue anchor relative to the needle such that the tissue anchor exits the needle lumen.

20. The method of claim 19, further comprising the step of fixing the suture relative to the tissue by:
engaging the retaining sleeve with the outer sheath;
positioning the retaining sleeve proximate the tissue with the suture extending through the second internal passageway;
placing the suture in tension;
engaging the plug with the inner sheath;
positioning the plug within the second internal passageway of the retaining sleeve such that the suture is compressed between the plug and the retaining sleeve.

21. The method of claim 20, further comprising the step of pulling the suture in a proximal direction while pushing the inner sheath and the plug distally, the inner sheath and the plug being pushed distally relative to the outer sheath and the retaining sleeve.

22. The method of claim 19, wherein the medical device includes a plurality of tissue anchors serially aligned within the needle lumen, and wherein the step of deploying the tissue anchor is repeated for at least a portion of the plurality of tissue anchors.

* * * * *